United States Patent [19]

Barber

[11] Patent Number: 4,862,877

[45] Date of Patent: Sep. 5, 1989

[54] HAND SPLINT FOR WRIST SUPPORT WITH OPTIONAL SUPPORT OF MP JOINTS AND THUMB AND IP FINGER ASSISTS

[75] Inventor: Lois M. Barber, Pismo Beach, Calif.

[73] Assignee: LMB Hand Rehab Products, Inc., San Luis Obispo, Calif.

[21] Appl. No.: 124,986

[22] Filed: Nov. 18, 1987

[51] Int. Cl.⁴ ............................................. A61F 5/04
[52] U.S. Cl. ..................................... 128/77; 128/85; 128/89 R; 272/67; 272/68
[58] Field of Search .................... 272/67, 68; 128/85, 128/87 R, 87 A, 89 R, 77; 2/DIG. 6

[56] References Cited

U.S. PATENT DOCUMENTS

| | | | |
|---|---|---|---|
| 248,980 | 11/1881 | Atkins | 272/67 |
| 1,817,212 | 8/1931 | Siebrandt | 128/85 |
| 2,312,523 | 3/1943 | Corbett | 128/85 |
| 3,057,354 | 10/1962 | Roberts et al. | 2/DIG. 6 |
| 3,063,749 | 11/1962 | Struble et al. | 2/DIG. 6 |
| 3,815,587 | 6/1974 | Guerrant | 128/77 |
| 3,938,509 | 2/1976 | Barber | 128/89 R X |
| 4,214,579 | 7/1980 | Ford | 128/94 |
| 4,341,331 | 7/1982 | McDougall | 224/222 X |
| 4,602,620 | 7/1986 | Marx | 128/77 |
| 4,677,971 | 7/1987 | Lindemann | 128/87 R |
| 4,719,906 | 1/1988 | De Prospero | 128/87 A |

FOREIGN PATENT DOCUMENTS 2576512  8/1986  France .................................. 272/67

OTHER PUBLICATIONS

Orthese de la Main, 10/1986.

Primary Examiner—Robert A. Hafer
Assistant Examiner—Kevin G. Ronney
Attorney, Agent, or Firm—George F. Bethel; Patience K. Bethel

[57] ABSTRACT

A hand splint which leaves the volar wrist free and which can be used alone or as a foundation splint for the attachment of various permanent and removable hand and finger corrective devices. The splint includes a manually bendable support medium having a substantially C-shape including a palmar piece which fits into the palmar arch of the hand, a proximal dorsal forearm piece adapted to contact the dorsal wrist and at least a portion of the dorsal forearm, and a dorsal hand piece extending between the palmar piece and the proximal dorsal forearm piece. Adjustable tension means is provided on the dorsal side of the wrist. Detachable thumb, finger and metacarpophalangeal support as well as an interphalangeal assist are provided separately and in combination. A novel hinge and adjustable strap attachment means are also provided.

34 Claims, 8 Drawing Sheets

HAND SPLINT FOR WRIST SUPPORT WITH OPTIONAL SUPPORT OF MP JOINTS AND THUMB AND IP FINGER ASSISTS

BACKGROUND OF THE INVENTION

1. Field of the Invention

This invention relates to the field of hand splints and especially to a hand splint which provides wrist support alone or can be used as a foundation for attachment of various hand, thumb and finger corrective devices. Embodiments show the basic splint coupled with an optional metacarpophalangeal (MP) support, thumb support, a MP extension stop with an interphalangeal (IP) assist and an adjustable thumb extension support and assist.

2. Description of the Prior Art

In recent years, numerous hand splints have been invented which constituted a major improvement over the wood and plaster splints commonly used in the past. The latter splints, while suitable for certain types of correction and straightening of bones were found to be quite unsuitable for the correction of problems unique to arthritic patients. These patients require more flexible and especially adjustable splints which enable the gradual urging of the bones back into the normal position, as well as adjustments to allow for swelling and/or pain.

Another requirement is to have a splint which can be easily put on and removed by such a patient. Other desirable features include washability, durability, light weight, and ventilation due to its open design.

Perhaps most important to the patient is a combination of comfort and at least partial use of the hand during wear. Comfort requires soft edges and surfaces to prevent pressure problems as well as enough exposure to air to minimize perspiration. Splint design must allow for the normal palmar arch of the hand. Also, support is desirable to hold the hand in both flexion-extension and radio-ulnar alignment. The thenar eminence (ball of the thumb) should be kept free if possible to permit movement of the thumb during wearing of the splint and the palmar support should be proximal to the palmar crease to allow full use of the fingers.

By virtue of the elastic dorsal wrist strap the wrist is not held rigidly and is permitted some freedom. The dorsal strap by its elastic nature assists the wrist back into extension.

Felt is often used as a cushioning material which does not permit washability or waterproof characteristics. The splint is thus limited to use around water since the felt will become wet and the metal parts subject to attack by moisture.

Furthermore, a flat piece of wire or steel is commonly utilized as the palm piece in prior art hand splints which do not accommodate the normal palmar arch of the hand resulting in a lack of comfort and function. In addition, flat wire and steel bands are too rigid to permit bending to provide a custom fit for each individual hand.

There are many different types of correction of the hand and fingers required in the treatment of hand injuries and those afflicted with arthritis and paralytic conditions. This has required great ingenuity on the part of occupational therapists and orthopedic doctors to provide just the proper amount of correction while maintaining use of the hand. This has given rise to many specialized splints, each designed to correct and treat a specific injury or condition.

SUMMARY OF THE INVENTION

The hand splint of the invention overcomes the deficiencies of the prior art by providing a splint which is light in weight, easily put on and taken off, and capable of individual custom fit by virtue of its bendable nature without the need of special tools.

Four separate splints are provided, each having in common the basic configuration of the simplest splint. The simplest form of the splint is designed to be used for wrist support and to act as a foundation for attachment of other hand, finger and thumb corrective attachments.

The basic splint includes a manually bendable support medium having a substantially C-shape. The upper end of the C-shape forms a palmar piece which fits into the palmar arch of the hand while the back of the C contacts and supports the radial side of the forearm while leaving the thumb free to move. The base of the C extends from the radial side across the dorsal or upperside of the forearm and extends to the wrist on the ulnar side of the forearm. The framework, preferably of a bendable wire, is enclosed in a soft cushioning material having novel strap attachment means.

As used herein and in the appended claims: Volar refers to the palm or underside of the arm or hand. Dorsal refers to the back of the hand or forearm. Ventral refers to the underside of the hand or forearm. Radial refers to the side of the hand and forearm on the side of the thumb. Ulnar refers to the side of the hand and forearm on the side of the little finger. IP refers to interphalangeal; MP refers to metacarpophalangeal; CMC refers to carpometacarpo; PIP refers to proximal interphalangeal; DIP refers to distal interphalangeal. Distal means farthest from the center of the body. Proximal means closest to the center of the body. Thenar eminence refers to the bulge at the base of the thumb. Carpus refers to the wrist.

Novel features of this invention include freeing of the volar and ulnar side of the wrist to permit desk-top activities. In addition, there is full thumb mobility and full finger mobility with the basic splint. This basic foundation splint is useful particularly for carpal tunnel syndrome, tendonitis, arthritis, wrist strain, post-wrist fracture and the like. Its highly ventilated design and light weight make it particularly comfortable to wear. Furthermore, the novel strap attachment means permits easy attachment, while the bendable framework permits easy adjustment by hand.

Using the basic splint as a foundation, one embodiment of the invention adds a thumb support which allows the thumb to be supported in an abducted position in front of the palm allowing prehension of the index finger pad against the thumb pad. The actual degree of flexion/extension can be determined by manual bending of the splint. This splint is indicated in many conditions such as paralysis in the case of quadraplegia, arthritis, post-fractures, tendonitis, joint strain and post-surgery.

The thumb support is also in the form of a bendable framework preferably a bendable wire in conjunction with a narrow piece of metal, such as an aluminum alloy. The thumb support is also covered with a padded material, preferably foam, for comfort.

Another embodiment of the invention using the basic splint as a foundation includes an additional transverse extension for volar support of the MP joints with an optional detachable malleable thumb support. The splint can be adjusted to provide the desired flexion/extension support to the MP joints and also supports the wrist.

The removable thumb support attaches to the splint preferably by means of conveniently placed areas of small hooks and brushed material. It can be easily adjusted and shaped by bending to support a painful thumb. It is useful for treatment of arthritis or tendonitis and also for post-tissue trauma, post-fractures, and post-surgery especially where wrist, MP joints, and thumb need support and rest.

The removable thumb support preferably has a framework formed of a single length of malleable wire, preferably aluminum, with an attached malleable piece of soft aluminum strip. The entire detachable thumb support is enclosed in foam or other cushioned material for comfort.

Another embodiment of the invention which incorporates the basic C-shaped splint as a foundation can be elongated along the radial side of the C-shape to provide additional support. Attached to the basic splint configuration is a dorsal MP extension stop. It is preferably formed as an extension from the palmar support upwardly and across the dorsum of the hand in the vicinity of the MP joints to contact, cover and follow the curve of the proximal phalanges of the fingers. A further dorsal extension upwardly and transversely in the opposite direction in a substantially U-shape provides a means of attachment for removable IP extension assists. An additional feature is the provision of a removable thumb support or assist.

The IP extension assists are each made up of a length of bendable wire looped at the distal end. Four of these wires are attached across the legs of the U-shaped member. A finger sling having elastic tension means attached thereto for spring extension of the IP joints is supported by the proximal leg of the U-shaped member and by the loop at the distal end of the bendable wire. Each elastic component is secured to the proximal end of the splint. Tension is modified for each elastic by length and size.

Each bendable wire finger component is adjustable for length by means of its method of attachment to the U-shaped member. Each wire can also be bent to be at the correct angle for assisting each finger into extension. After the desired position is determined, the wire can be cut adjacent to the proximal wire of the "U" to give a neater appearance.

This splint with removable thumb support and removable IP extension assists is useful particularly for nerve injuries, crush injuries, post fractures, post surgery, post burns, and the like.

In the basic foundation splint and in each embodiment the splint is secured to the hand and forearm by securement means which are preferably in the form of detachable straps. The straps are preferably of an elastic stretchable material secured by means of hooked areas in conjunction with interlocking brushed material.

A particular feature of the invention is a novel hinged lock for securement of the straps to the splints. The novel hinge includes either a plurality of small hooks or a brushed material on at least one of its interior sides. The hinge interlocks with an area of brushed material or a plurality of small hooks respectively on a strap.

In its most preferred form, the basic splint is made of a single length of bendable wire such as aluminum which is strong yet easily adjusted to the individual needs of each patient.

When it is necessary to attach two pieces of wire, they are preferably joined by means of a sleeve, preferably of plastic such as Tygon TM tubing. This material not only provides a strong attachment, but also the capability of rotation as well.

The framework is preferably enclosed in a soft piece of foam cushioning preferably in the form of a sandwich. This can be any type of material but is preferably a heat-sealed, closed cell polyethylene foam, which provides support and comfort during use. The preferred material, foam plastic, is waterproof and washable which further increases its convenience and desirability.

The fastening straps are preferably stretchy and are capable of easy adjustment relative to the snugness of the attachment across the dorsal wrist and across the ventral forearm and dorsal hand area. These straps are designed for the easy one hand attachment and detachment to the splint. This is especially appreciated by arthritic patients who commonly have limited use of their hands and fingers and find most fasteners difficult to operate.

The arrangement of the straps is designed to distribute the pressure of attachment while at the same time preventing slipping of the splint on the hand.

The splint must be customized in order to fit the right or left hand. A right and left hand splint constitute mirror images of each other. Various sizes of the splint can be made to fit different sized hands. Furthermore, the inner malleable wire framework permits custom fitting of the splint to each hand without special tools. This is especially useful to accommodate any changes in the hand due to any correction thereof or to other changes such as swelling.

Since the exterior cushioning material is soft and washable, activities such as showering and other water related action can be engaged in without damaging the splint.

If additional wear resistance is required either on the dorsal or ventral side of the splint, an additional layer of abrasion resistant sheeting such as leather or vinyl can be adhered to the cushioning material without departing from the spirit of the invention.

BRIEF DESCRIPTION OF THE DRAWINGS

The invention will be more clearly understood by reference to the description below, taken in conjunction with the accompanying drawings wherein.

DETAILED DESCRIPTION OF THE INVENTION

Figure 1:
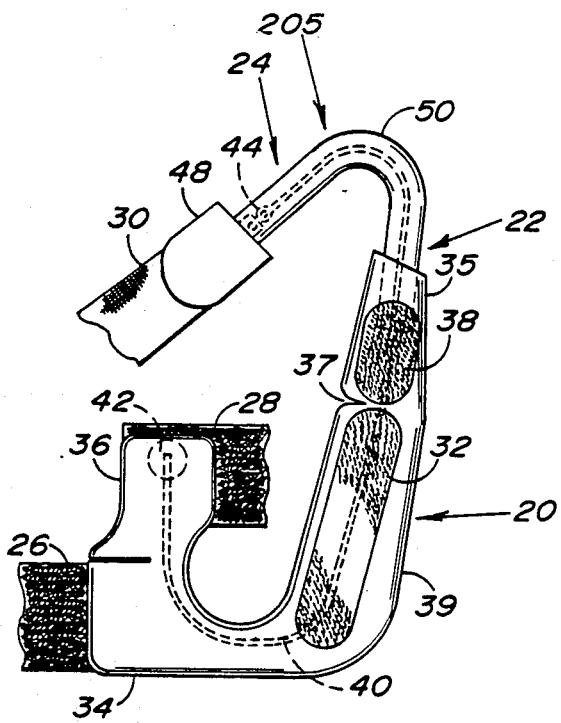
FIG. 1 shows a plan view of the exterior exposed side of a left hand basic foundation splint of the invention in a flattened configuration.

The basic splint of the invention is embodied particularly in FIGS. 1 through 5 and is indicated by 205. This splint 205 serves as a basic splint to which other types of hand and finger correcting splints can be attached. In the following description, like pieces contain like numbers for all the figures.

It should be noted that while a left hand splint is shown in the drawings it should be understood that a right hand splint is the mirror image of the left hand splint.

Figure 2:
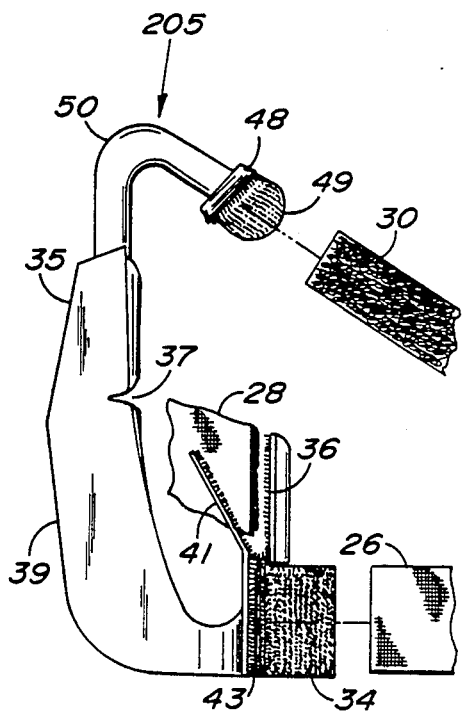
FIG. 2 shows a plan view of the contact side of the a left hand basic foundation splint of FIG. 1 in a flattened configuration.
Figure 4:
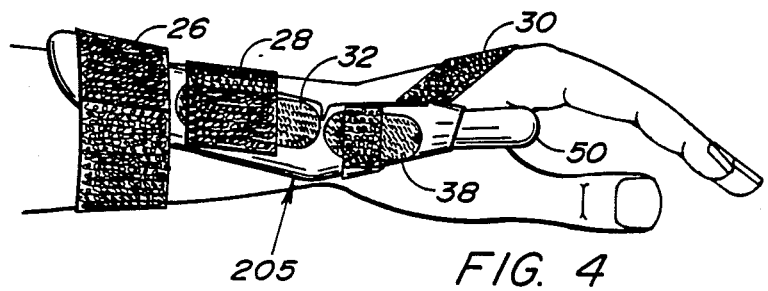
FIG. 4 shows the left hand basic foundation splint of the invention in use as viewed from the radial side of the hand.
Figure 5:
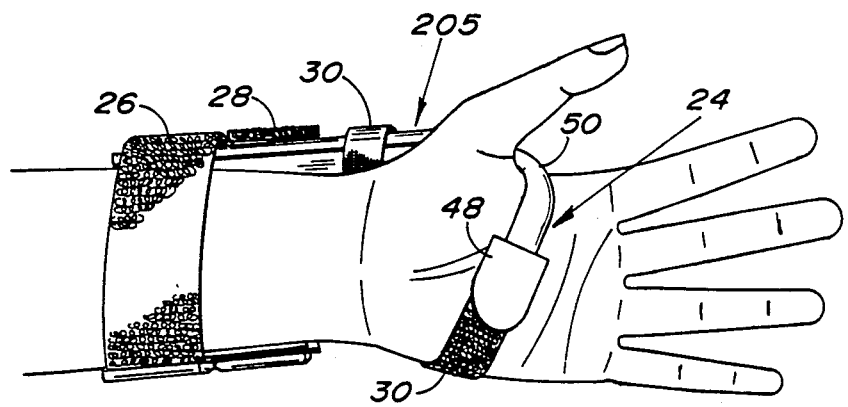
FIG. 5 shows the left hand basic foundation splint of the invention from the volar side of the hand.

FIGS. 1 and 2 show the splint in a flattened condition. In actual fact, as shown in FIGS. 4 and 5, the foam cups and conforms to the forearm in its finished state.

Referring now to FIG. 1 of the invention there is shown the basic foundation splint 205 which is useful by itself as a wrist splint but which is also a foundation splint for the attachment of various hand, finger and thumb correction attachments.

As shown, it includes a proximal dorsal forearm section 20 which is attached to a dorsal hand section 22 which in turn is connected to a palm piece 24. In its most preferred embodiment, the framework 40 of the basic foundation splint 205 is made of a single length of bendable wire, such as aluminum. As shown in FIGS. 1 and 2, the splint 205 has a substantially C-shape. The base of the C-shape which forms the proximal dorsal forearm section 20 is somewhat U-shaped.

It can be seen that the framework 40 is enclosed in a sandwich of cushioning material 39 which encloses the proximal dorsal forearm section and extends partially to the dorsal hand section 22. The remaining portion of the dorsal hand section 22 and the palm piece 24 are surrounded by rubber tubing 50.

The splint 205 is attached to the arm and hand by means of preferably soft, cushioned elastic straps. The splint 205 provides a unique hinged lock as a means of securing the splint to the hand and forearm.

Figure 3:
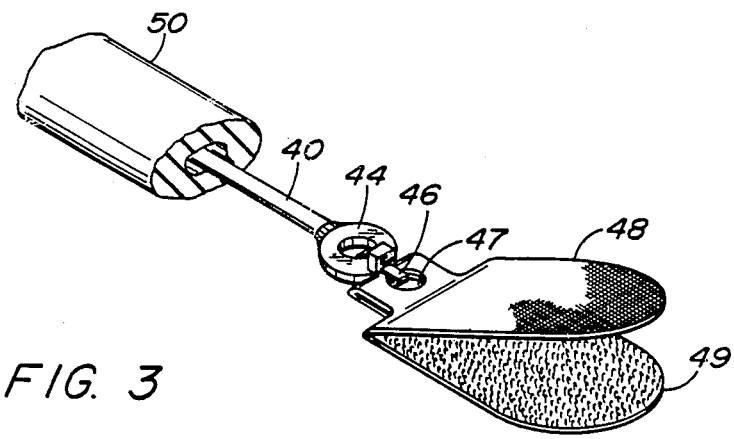
FIG. 3 shows an enlarged somewhat perspective view of the hinged strap attachment on the palmar piece of FIG. 2.

As shown particularly in FIGS. 1, 2 and 3, a strap 30 for the palm piece 24 includes a flexible hinge 48, the interior 49 of which is covered on both sides with a plurality of small hooks preferably of plastic which engage and interlock with brushed material on the exterior of strap 30.

As detailed in FIG. 3, the end of the wire framework 40 is flattened into a loop 44. The flexible hinge 48 contains an aperture 47 through which a cable lock 46 is passed to anchor the hinge to the loop 44 of the wire 40. Thus, the cable lock 46 unites the framework 40 to the hinge 48.

While the hinge 48 is shown with small hooks interiorly and the strap 30 includes a brushed material for engagement with the hooks, it should be understood that the opposite arrangement can also be employed. That is, the hinge 48 can contain brushed material in place of the hooks 49 and the strap 30 can include the hooked section if desired.

The advantage of the hinge 48 is that it is flexible, extremely strong, low in profile, light in weight and easily attached and detached and acts to protect unfinished strap ends. In addition, it is not bulky and does not provide any irritating substance next to the skin of a patient.

A pair of similar hinged locks are found on the proximal dorsal forearm section on the ulnar side of the splint 205.

As shown, particularly in FIGS. 1 and 2, hinge 36 contains two adjacent sides having interiorly adhered small hooks 41 which engage a wrist strap 28. The wrist strap 28 is made of an elastic brushed material which engages the hooks 41 within the hinge 36.

In order to provide greater comfort to the wearer, the framework 40 of the basic splint 205 is preferably contained in the upper and outer portion of the hinge 36 and includes between the hooked areas 41 a small cushioned pad 42 which overlies the end of framework 40 between the foam 39 and the hooks 41.

In a similar manner but opening in a direction 180° from the hinge 36 is hinge 34 which, as shown in FIG. 2, is provided with a plurality of small hooks 43 on its interior facing sides. The hooks 43 engage brushed material on straps 26.

In the hinges 34, 36 and 48 the area of hooks can be replaced with a brushed material and the strap can be provided with a plurality of small hooks without departing from the invention. Similarly, one of the interior facing sides of the hinge can be provided with a plurality of small hooks and the other facing side be provided with brushed material. It can then be adhered to a strap having one side provided with brushed material and the other side provided with a plurality of small hooks for engaging the respective hooks and brushed material of the hinge.

The advantages of these hinged locks 48, 36 and 34 are mainly that they are soft and flexible to conform to the contours of a hand or arm. Furthermore, the strength provided is coupled with an exterior protective surface and the ability to engage one or both sides of brushed strap material. It is of particular advantage in making personal adjustment of the splint 205 to an individual since the strap material can be cut to size so as to eliminate extraneous material.

With respect to the straps, it should be noted that the foundation splint 205 is primarily attached to the arm by means of the strap 26. As mentioned previously, one end of the strap 26 engages hooks 43 within hinge 34 and the other end engages hooks on patch 32.

Dorsal wrist strap 28 performs an entirely different function and is not utilized to attach the foundation splint 205 to the arm. It extends only across the back of the wrist and is present to provide a wrist extension support and assist. One end of the preferably brushed soft elastic material is engaged by hooks 41 of hinge 36 and the other end is adhered to patch 32 containing a plurality of small hooks. Thus, it is adjustable to provide the desired tension against the wrist extension.

The palm piece 24 with the hinge 48 engages the brushed material of strap 30 at one end and is attached to the splint at its other end by engagement with hooked patch 38. As shown in FIG. 4 this strap extends diagonally across the back of the hand and is preferably slipped under the material of the splint 205 prior to engagement with patch 38. This manner of the engagement of the strap is optional but provides the advantage in that it can be used to pull the splint 205 away from contact with the hand.

As mentioned previously, the splint 205 is made of a bendable material which is preferably aluminum wire although other materials can be used as well.

It should be noted that there is a slot 37 in the outer foam covering which is approximately midway between the palm piece 24 and the base of the splint. This is located at approximately the end of the radius bone of the forearm. This is to permit bending of the splint 205 at this point so that the foam covering 35 does not interfere with the adjustability of the splint. In general, it is desirable to bend the splint 205 at this point upwardly relative to the longitudinal axis of the arm to provide a slight extension to the wrist. A neutral position or an extended position of the wrist may be indicated depending on the condition and the philosophy of the physician.

As mentioned above, the palm strap 30 is preferably wrapped reversely around the splint to prevent pressure of rotation inwardly of the hand, although this is an optional method of attachment.

With respect to the palm piece 24, it should be noted that it follows the curve of the distal palmar crease and palmar arch of the hand. The rubber covering provides durable wear as well as cushioning. Foamed material can also be used and is preferred in the other splint embodiments.

Splint 205 is particularly advantageous in that the volar side of the wrist is kept free and it prevents pressure problems which are encountered with other prior art splints. The exposure of the volar and ulnar wrist allows contact of the skin with desk and work surfaces giving sensory feedback. At the same time the hand can bend a little bit and the splint 205 can be adjusted to provide individual comfort. The stretchiness of the straps also provides increased comfort. At the same time, the splint 205 permits full finger and thumb movement while being worn.

As noted above, substantially all of the basic foundation splint 205 with the exception of the palm piece 24 is enclosed preferably in a sandwich of pliant cushioning material 35, preferably a heat-sealable polyethylene foam or equivalent material. Preferably, such cushioning material is waterproof and provides sufficient cushioning of the framework 40 of the splint.

Other types of foam can be used, such as for example, polypropylene foam, ionomer foam, polystyrene foam, polyurethane foam, PVC (polyvinylchloride) flexible foam and silicone foam. The above mentioned plastic foams are intended to be exemplary and are not intended to in any way limit the type of cushioning material which can be used in the invention. Not all of the above mentioned foams are capable of being heat sealed and might require adhesive to improve the bonding of the foam layers together. This should in no way limit the use thereof.

The main advantages of the use of polyethylene foam include the characteristics of low water absorption, good energy absorption, water vapor barrier, compressability, smooth surface, thermal stability at temperatures up to 215° F. and a high ratio of tensile and shear strength to weight compared to other resilient foams. In addition, the capability of being heat sealed also makes it additionally attractive. While rubber tubing is used in the basic splint of the invention, this can also be substituted by the use of foam as used in the other embodiments of this splint.

With respect to the straps 26, 28 and 30, they are preferably provided in the form of a soft elastic brushed material which engages hooked areas as noted above. This provides for the easy attachment and detachment of the straps which is difficult for persons since most likely only one hand is available to accomplish this task. At the same time, there is provided the capability of considerable adjustment due to different hand and forearm size, as well as transient changes in hand size due to swelling and other causes which can vary over time.

Although the straps have been shown to be composed of a padded brushed nylon material which also has preferably an elastic characteristic which attaches in conjunction with hooked areas, other types of fastening means can also be used. For example, such hooked patches can be sewn to cotton straps, or in place of the hooked patches, there can be substituted buckles, snaps, buttons, hooks and the like. However, these materials are not as preferred, since they do not provide the easy adjustment which is obtainable for the use of the hooked patches with the brushed material.

The basic foundation splint 205 as described and shown in FIGS. 1 through 5 is distinguished from the embodiments shown in the remaining figures by the additional hand and finger attachments.

Figure 6:
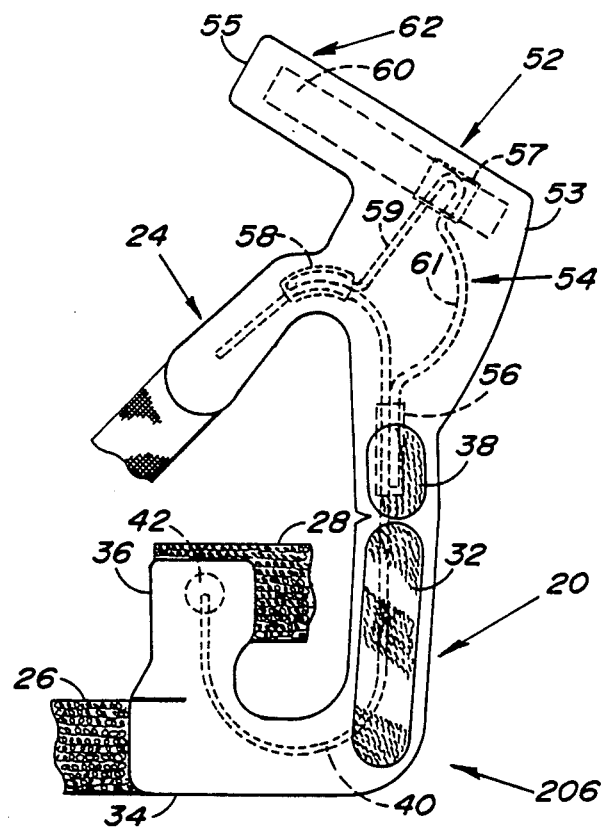
FIG. 6 shows another embodiment of the left hand basic foundation splint in a flattened configuration which incorporates a thumb extension support.
Figure 7:
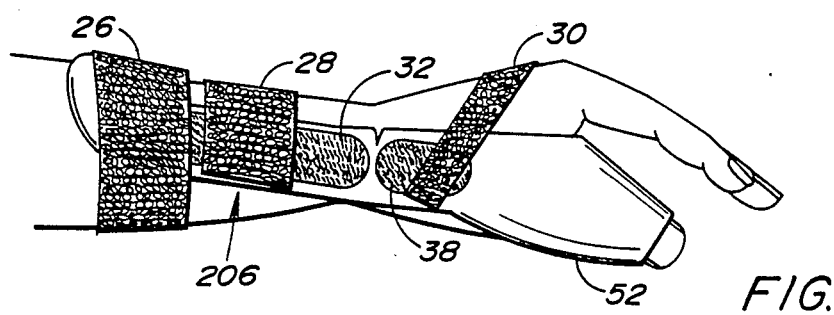
FIG. 7 shows the left hand splint of FIG. 6 in use on a hand as viewed from the radial side of the hand.
Figure 8:
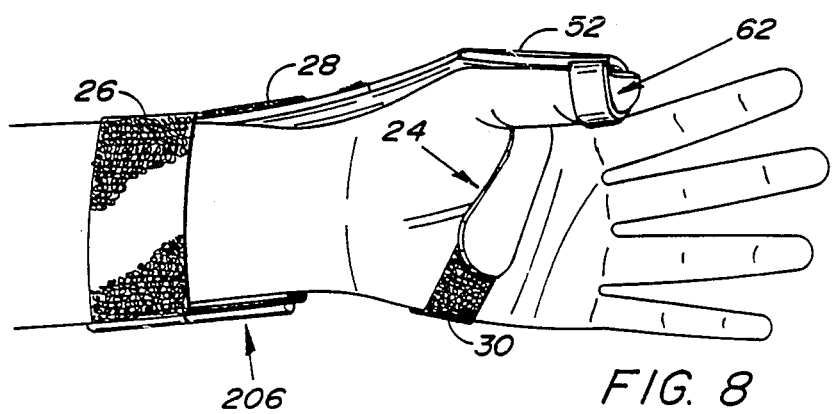
FIG. 8 shows the left hand splint of FIG. 7 from the volar side of the hand.

The splint 206 of the invention as shown in FIGS. 6, 7 and 8 incorporates the basic foundation splint 205 of FIGS. 1 through 5 and adds an integral thumb support 52.

FIG. 6 shows splint 206 in a flattened configuration. When the foam material is used to enclose the framework 40 it is held in the cupped configuration after heat sealing which permanently sets it in place. This still allows for a certain amount of rotation about the wire framework, if desired, which gives some leeway in adjustment for different sizes.

It should also be mentioned that the splints of the invention can be made in different sizes with respect to length as well as width without departing from the invention. Also, while a left hand splint is shown in the drawings, a right hand splint would constitute a mirror image thereof.

It can be seen in the splint 206 of FIG. 6 that a thumb support 52 is added to the basic splint 205 shown in FIGS. 1 through 5. A foam padding over the palm support piece 24 replaces the rubber tubing. In other respects, the basic portion of the splint 206 is the same as splint 205 shown in FIGS. 1 through 5.

The thumb support 52 of splint 206 includes a thumb support wire frame 54 which is attached to the wire frame 40 of the basic splint by means of Tygon TM tubing 58 and 56. This holds the thumb support 52 tightly in contact with the wire frame 40. The thumb support wire 54 as shown in FIG. 6 has a somewhat b-shape. Extension 59 of the thumb support wire frame 54 generally follows the line of the thumb with respect to its longitudinal axis while extension 61 is designed to follow the thenar eminence of the thumb. The two extensions 59 and 61 are secured to a malleable aluminum strip 60 designed to surround the distal end of the thumb. This is accomplished by means of shrink fit tubing 57 through which the frame 54 is inserted.

The fastening of the splint with respect to the straps is exactly as for the basic foundation splint of FIGS. 1 through 5. This splint 206 is particularly designed to treat a condition where there is an inflammation of the thumb, especially, for example, de Quervain's syndrome, as well as for treatment of paralysis (as in the case of quadriplegia) arthritis, post fractures, tendonitis, joint sprain and post surgery, and other conditions involving the thumb and the wrist.

The IP joint of the thumb can be confined or movement can be allowed, depending upon the adjustment of the distal end of the thumb piece 62.

The splint 206 supports the wrist in the desired position as determined by bending of the frame upwardly at 37. The thumb is supported in an abducted position in front of the palm allowing prehension of the index finger pad against the thumb pad.

The hinge lock 48 of the palmar piece 24 differs from basic splint 205 of FIGS. 1 through 5 in that the hinge 48 is not physically attached to the end of the wire frame 40. The exterior is simply covered with the foam material which covers the rest of the splint. In other respects, the function is exactly the same.

The next embodiment of the splint 205 is splint 207 shown in FIGS. 9 through 13. The construction is essentially the same as for the basic splint 205 of FIGS. 1 through 5 but in addition supports the MP joint in the desired flexion-extension. There is also an optional malleable removable thumb support which is designed to be removably attached to the basic splint. This can be adjusted to support a painful thumb. In addition, the thumb piece is easily shaped. It is not intended for the active hand.

This splint 207 is particularly suited for arthritis or tendonitis and also for post-tissue trauma, post fractures, post surgery, where wrist, MP joints and thumb need support and rest. It is preferably provided with a long middle strap to support the volar wrist if necessary.

Figure 9:
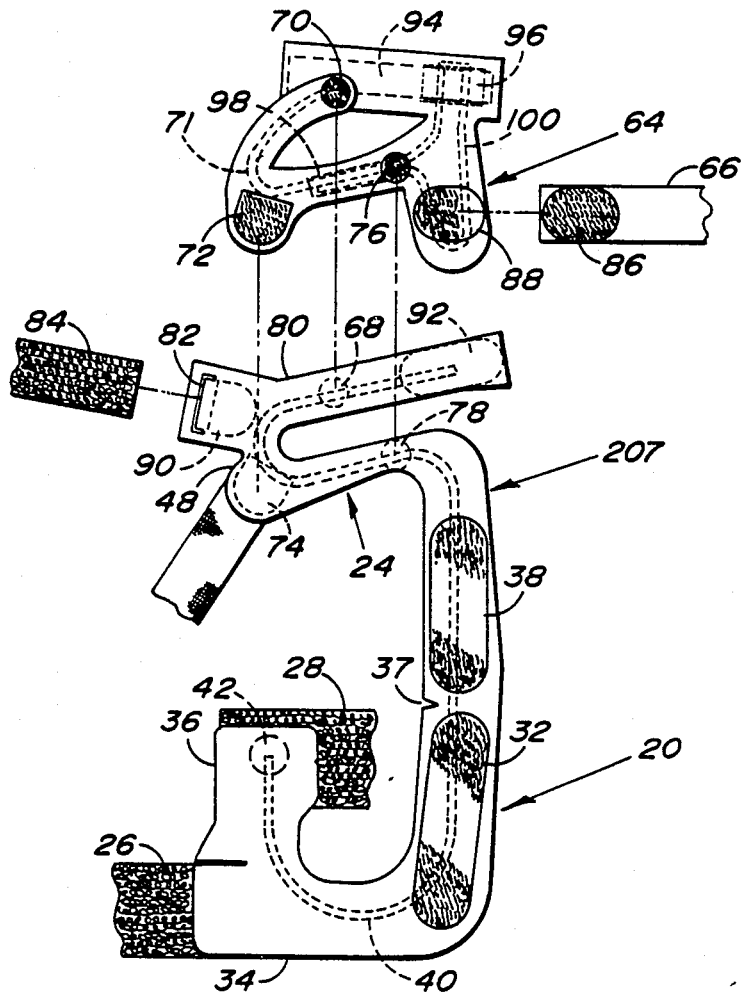
FIG. 9 shows another embodiment of the foundation splint of the invention for a left hand which includes a transverse extension for volar support of the MP joints with a detachable thumb support.
Figure 10:
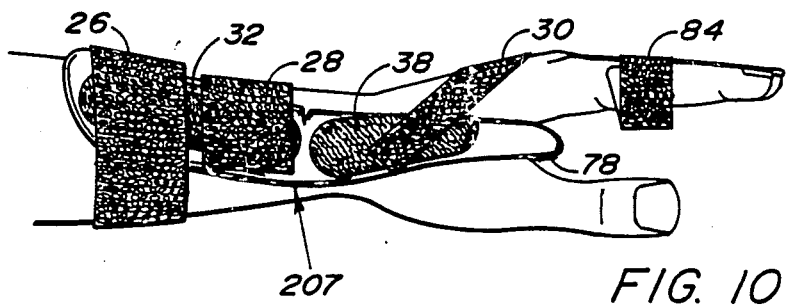
FIG. 10 shows the left hand splint of FIG. 9, without the detachable thumb support, in place on a hand as viewed from the radial side of the hand.

The splint 207 is shown in its flattened and broken away form in FIG. 9. It can be seen that this embodiment of the splint includes an extension attached to the palm support 24 in the form of a transverse extension 80 which provides for MP joint support. The MP joint support 80 is also enclosed in foam or other cushioning material as for the remainder of the splint. In addition, it includes a strap 84 preferably of a brushed material which adheres to hooked patch 90 and passes through slot 82 for dorsal hand contact as shown in FIG. 10. It attaches on the opposite end of the MP support 80 to hooked patch 92.

Figure 11:
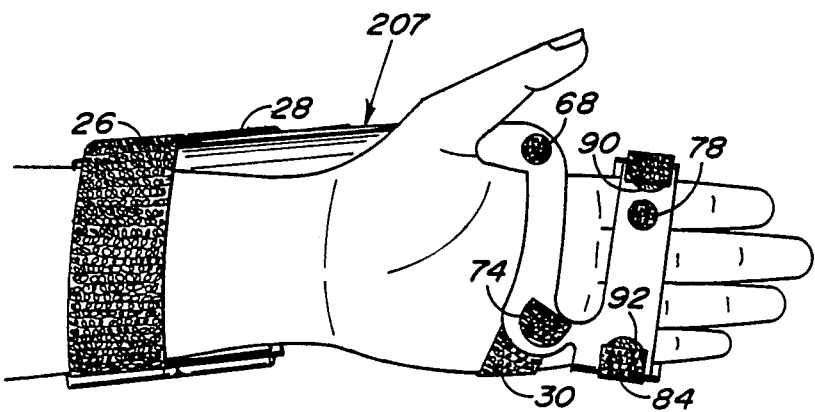
FIG. 11 shows the left hand splint of FIG. 9 without the detachable thumb support as viewed from the volar side of the hand.

The strap 30 for attachment to the hinge lock 48 is substantially the same as for the other splints. FIGS. 10 and 11 illustrate the splint 207 with the removable thumb support 64 removed.

As shown in FIG. 9 the removable thumb support 64 includes as a framework a length of malleable wire 100 bent to provide support to the thumb. One end is secured to itself by means of a length of Tygon TM tubing 98. The remaining end is bent to conform generally to the configuration of splint 207. A strip 94 of malleable metal, preferably of aluminum is attached to the wire framework 100. When in use, the strip 94 is bent to a generally circular configuration to support the distal end of the thumb. The framework is preferably enclosed by a sandwich of foam 71.

Figure 12:
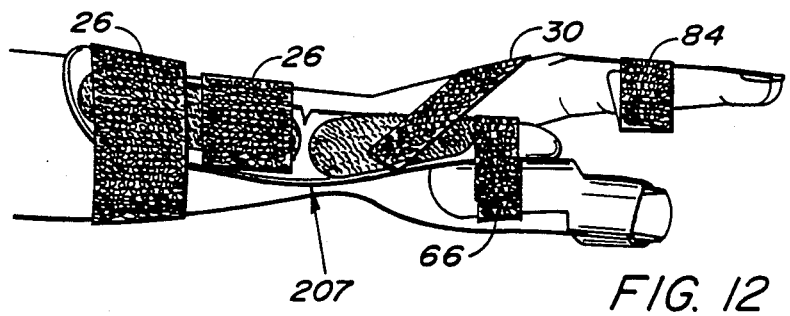
FIG. 12 shows the left hand splint of FIG. 9 with the removable thumb support attached as viewed from the radial side of the hand.
Figure 13:
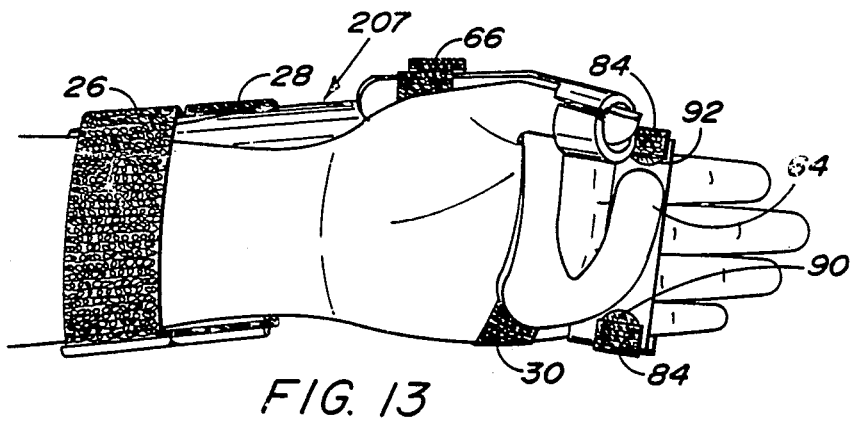
FIG. 13 shows the left hand splint of FIG. 9 with the removable thumb support attached as viewed from the volar side of the hand.

FIGS. 12 and 13 show the splint 207 with the removable thumb support 64 attached.

The removable thumb support 64 attaches to the splint by means of hooked patches in conjunction with brushed material patches. Thus, hooked patch 72 on the thumb support 64 engages brushed patch 74 on the end of the palmar support 24. Similarly, hooked patch 70 engages a brushed patch 68 on the MP support 80 and hooked patch 76 engages a brushed patch 78 on the palmar support 24.

In addition, a strap 66 having a hooked patch 86 provides additional stability. The strap 66 is wrapped around the splint and the removable thumb support. The underside of the strap 66 engages hooked patch 88 and is wrapped around the splint to engage its own hooked patch 86. This prevents the removable thumb support 64 from moving when in use.

The final embodiment is splint 210 shown in FIGS. 14 through 17. This embodiment includes the basic foundation splint 205 with an extension of the palmar piece 24 which is a dorsal transverse extension 111. It is comprised of a manually bendable dorsal proximal phalangeal piece which is adapted to contact, cover and follow the curve of the proximal phalanges of the fingers. It acts as an MP extension stop. It is entirely enclosed and cushioned by a pliant cushioning material, preferably polyethylene foam.

Figure 17:
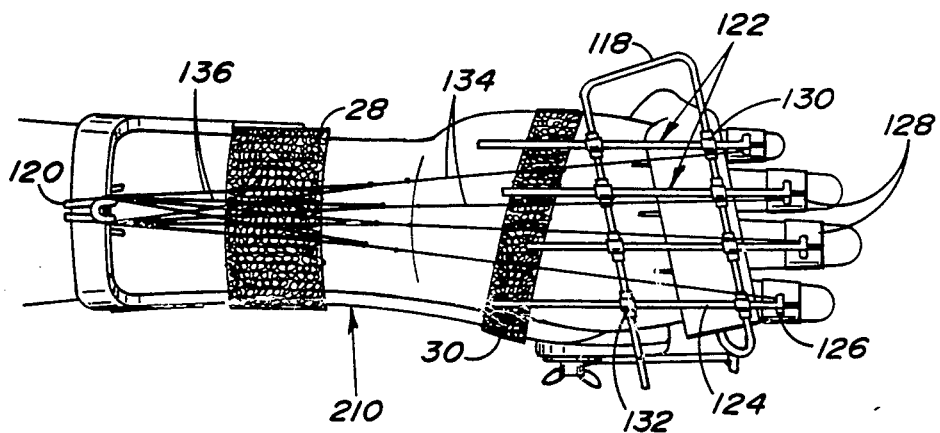
FIG. 17 shows the splint of FIG. 16 as viewed from the dorsal side of the hand and details the IP extension assist outrigger mechanism.

A further transverse dorsal U-shaped extension 118 forms the basis of the attachment of outriggers 122 as indicated in FIG. 17.

In addition, the splint 210 also is provided with a removable thumb support or assist 138.

This splint is particularly useful for treatment of nerve injuries, crush injuries, post fractures, post surgery, post burns and the like.

Figure 14:
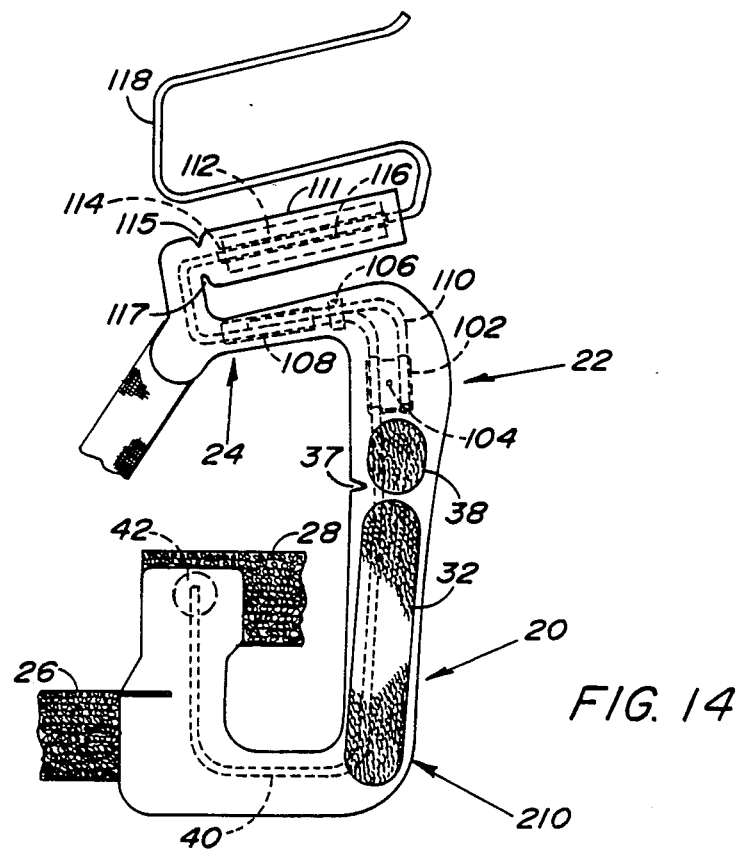
FIG. 14 shows another left hand embodiment of the invention in its basic flattened configuration.

As can be seen in detail in FIG. 14, the dorsal proximal phalangeal (PP) extension 111 which acts as an MP extension stop includes a wire 116 which is enclosed by a section of Tygon TM tubing 114. An underpad 112 provides additional cushioning between the outer foam sandwich and contact with the hand.

A particular feature of the MP extension stop 111 is the fact that it rotates slightly with respect to the inner frame wire 116. This is made possible by V cuts 115 and 117 in the outer foam and the fact that the pad and foam are attached to the Tygon TM tubing 114 which slips around the frame wire 116. This provides increased comfort and adjustment when the outriggers 122 are incorporated in the splint.

As shown in FIG. 17 the substantially U-shaped transverse dorsal extension 118 provides spring tension as well as a means of attachment for outriggers 122. Each outrigger 122 is comprised of a bendable wire 124 having an end loop 126. Each of the wires 124 are attached to U-shaped transverse dorsal extension 118 by means of two short lengths of Tygon TM tubing 132 one of which encircles each leg of the U-shaped member.

Figure 18:
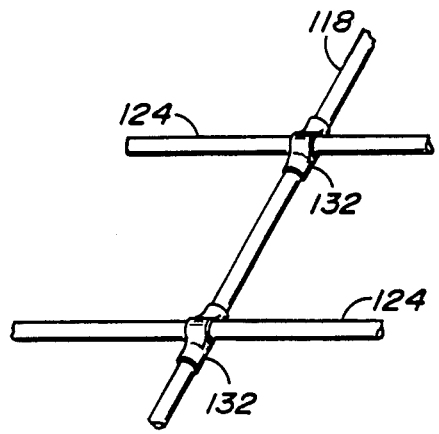
FIG. 18 shows an enlarged detail of the attachment of the looped wires to the transverse dorsal extension shown in FIG. 17.

FIG. 18 shows a detail of how each section of wire 124 fits through the Tygon TM tubing 132. As shown, a short section of Tygon TM tubing 132 is slipped over each of the legs of extension 118. A portion of the tube 132 is pulled upwardly from the leg of extension 118 and two apertures are made therein through which the wire 124 is passed. Under this condition, the wire 124 crosses each of the legs of extension 118 at approximately a 90° angle.

It should be noted that each of the wires 124 can be moved along its length backward and forward through the Tygon TM tubing 122 for adjustment. At the same time, each of the Tygon TM tubing sections 132 are movable along each leg of the extension 118. This also permits more individual fit for each individual patient. If desired, one or more of the wires 124 can be removed.

In addition to the wires 124 containing end loops 126, the outriggers 122 also include loose fitting loops or slings 128, preferably made of leather which hold each of the fingers. The slings 128 are provided with apertures 129 through which a string 134 is secured. The string 134 is threaded through end loop 126 of respective wire 124. Each string 134 is attached to an elastic band 136 which is looped around clip hook 120 which is secured to the end of the splint 210.

It can be appreciated that the actual tension on each of the loops or strings 128 is adjustable by the length and thickness of the rubber band 136 and the length of the strings 134.

Splint 210 also includes a removable thumb support 138. The thumb support 138 is attached to the basic splint as indicated in FIG. 14 by attachment to an aluminum strip 102 having an aperture 104. The aluminum strip 102 is secured to a parallel wire 110 which is secured at its opposite end to framework 40 on the palmar arch extension 24. The two wires are secured together by means of a length of Tygon TM tubing 108 which surrounds both wires and an aluminum strip 106 which surrounds the two wires as well.

Figure 20:
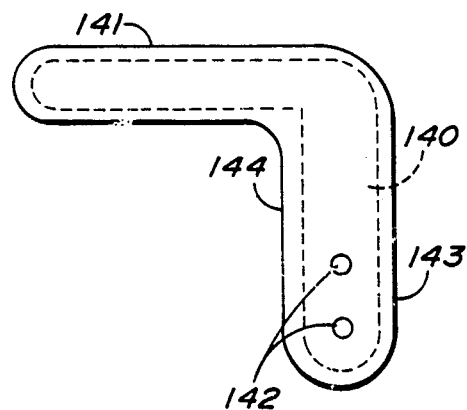

The thumb support 138 is detailed in FIG. 20. It includes an aluminum framework strip 140 having at one end one or more apertures 142. The entire strip 140 is surrounded by foam 144 in a sandwich arrangement as for the rest of the splint.

Figure 19:
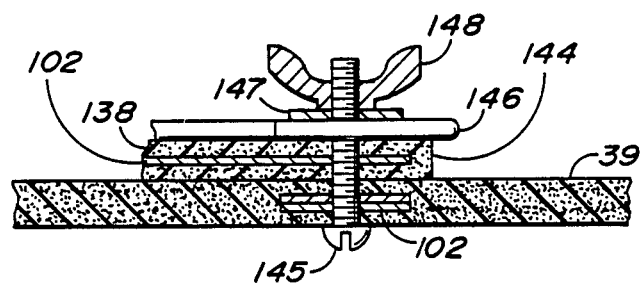
FIG. 19 shows an enlarged detail of the securement means for the detachable thumb support shown in FIG. 17; and, FIG. 20 shows the detachable thumb support of the splint shown in FIGS. 14–17 in a flattened configuration.

The thumb support has a substantially L-shape. As shown in cross section in FIG. 19, one leg 143 is secured to the splint by means of a bolt 145. Bolt 145 passes through the foam 39 of the body of the splint 210 through aperture 104 in aluminum strip 102. Then it passes through the foam 144 of the finger support 138, through aperture 142 of strip 102, through the opposite layer of foam 144, through the U-shaped end of wire 146 and finally through washer 147. The entire arrangement is then secured by means of wing nut 148.

Figure 15:
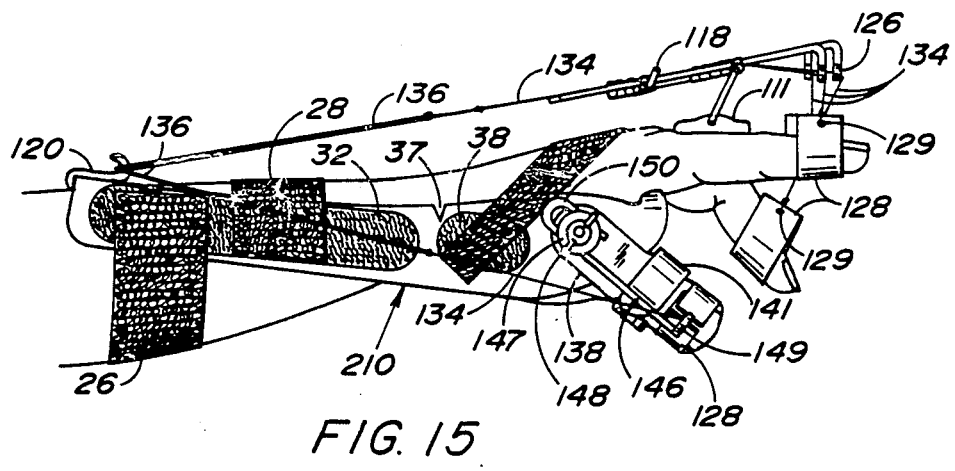
FIG. 15 shows the left hand splint of FIG. 14 on a hand as viewed from the radial side of the hand having attached a removable thumb support and removable IP extension assists.
Figure 16:
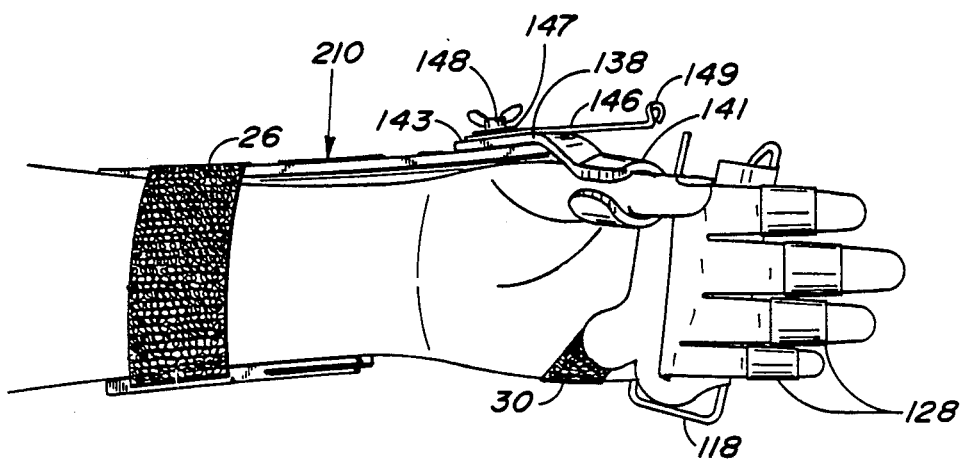
FIG. 16 shows the left hand splint of FIG. 15 on a hand as viewed from the volar side of the hand with the thumb loop removed.

Leg 141 of thumb support 138 is bent to encircle the thumb as shown in FIG. 15.

A sling 128, preferably of leather, is secured to a string 134. The string 134 is threaded through the looped end 149 of thumb wire 146. It is also attached by means of an elastic band 136 to end clip 120 as for the finger outriggers.

The U-shaped end 150 of thumb wire 146 is slidably secured by means of washer 147 and wing nut 148 for adjustment to accommodate varying lengths of thumb and for individual adjustment. Also, the thumb wire 146 and sling 128 can be removed if desired. This is also the case with the entire thumb support 138.

As described above, the basic foundation splint 205 described in FIGS. 1 through 5 can be modified by attachment according to the needs of the patient for example to provide thumb support as in 206, a removable thumb support in conjunction with MP support as in 207 as shown in FIGS. 7 through 13, and provided with a removable thumb support and an outrigger arrangement in conjunction with an MP extension stop as shown in the splint 210 shown in FIGS. 14 through 17.

The materials of which the splints are constructed permit individual adjustment without requiring special tools. While the preferred support material is an aluminum wire because of its light weight, low cost and malleable characteristics, other types of metals can be substituted therefor. Such metals should be light weight reinforcing metals which provide the strength and malleable characteristics of aluminum, such as for example among others, copper, steel, brass, and the like.

In place of metal, there could also be used a malleable type of plastic such as a malleable resilient type of natural or synthetic rubber or a metal reinforced plastic.

The splint has been designed to accommodate the normal alignment of the hand and wrist. For example, the placement of the palm piece is in alignment with the palmar crease. Similarly, the MP extension stop and the transverse MP support are disposed at an angle with respect to the joints of the hands which lie at a slight angle from the radial side of the hand to the ulnar side of the hand.

The combination of the small hooks and brushed material for attachment of the splint as well as for adjustment of tension on the splint is easily done. Thus, the splint is easily put on and taken off which encourages the use thereof. Also, since the splint only minimally restricts normal hand movement during use, the patient is also encouraged to wear it.

It should also be kept in mind that the malleable nature of the splint permits bending to accommodate the particular injury to be treated.

Various modifications of the invention are contemplated which would be obvious to those skilled in the art. For example other attachments to the basic foundation splint 205 are contemplated including the attachment of other types of hand and finger corrective devices not shown in this application and can be resorted to without departing from the spirit and scope of the invention as defined by the following claims.

I claim:

1. A hand splint which does not contact the volar wrist and which can be used as a foundation for the attachment of various permanent and removable hand and finger corrective devices comprising:

a manually bendable support framework with a pliant cushioning material enclosing at least a major portion of said framework;

said splint having an ulnar and a radial side corresponding to the contact of the splint with a forearm and comprising as major pieces;

a palmar piece adapted to extend under and across the palmar arch of the hand;

a proximal dorsal forearm piece adapted to contact the dorsal wrist and at least a portion of the dorsal forearm;

a dorsal hand piece extending between said palmar piece and said proximal dorsal forearm piece and adapted to contact the radial side of the hand and forearm;

said splint having a substantially "C" shape;

the top of the "C" including the palmar piece;

the back of the "C" adapted to extend along the radial side of the arm and including the dorsal hand piece;

the base of the "C" forming the proximal dorsal forearm piece and including a portion of the back of the "C" forming a radial extension adapted to extend along the radial side of the arm, a transverse extension adapted to extend across the dorsal forearm, and an ulnar extension adapted to extend along the ulnar side of the arm toward the dorsal wrist;

means for holding said major pieces together;

securement means for securing said splint to a hand and forearm without contacting the volar wrist; and, means to provide adjustable tension between said proximal dorsal forearm piece and said ulnar extension and adapted to contact the dorsal side of the wrist.

2. A splint as claimed in claim 1 wherein:

said framework is formed of a single length of malleable wire;

and said means to provide adjustable tension between said dorsal forearm and said ulnar extension which is adapted to contact the dorsal side of the wrist comprises an adjustable dorsal strap attached between said radial and ulnar extensions.

3. A splint as claimed in claim 2 wherein said securement means comprises:

adjustable strap means extending ventrally across the proximal end of said proximal forearm piece and secured between said radial and ulnar extensions; and, adjustable strap means secured to said palmar piece and adapted to extend diagonally across the dorsal side of a hand from said radial side to said ulnar side and secured to said dorsal hand piece.

4. A splint as claimed in claim 3 wherein:

said strap means are comprised of an elastic strap;

at least one area having a plurality of small hooks adapted to engage brushed material adhered to at least one of said strap and said palmar piece, dorsal hand piece, and proximal piece; and, at least one area of brushed material adapted to engage a plurality of small hooks adhered to at least one of said strap and said palmar piece, dorsal hand piece, and proximal piece;

and wherein, said palmar piece strap means extends under said dorsal hand piece prior to securement thereto to pull the dorsal hand piece slightly away from contact with the hand.

5. A splint as claimed in claim 3 wherein said strap means further comprises:

a first lightly padded flexible hinge having two facing interior sides, at least one interior side being covered with a material selected from a plurality of small hooks adapted to engage the brushed material on a strap and brushed material adapted to engage a plurality of small hooks on a strap;

said first hinge being attached to the distal end of said palmar piece;

a second lightly padded flexible hinge having two facing interior sides, at least one interior side being covered with a material selected from a plurality of small hooks adapted to engage the brushed material on a strap and brushed material adapted to engage a plurality of small hooks on a strap;

said second hinge being attached to the proximal dorsal forearm piece adapted for securing said splint around the ventral forearm;

a third lightly padded flexible hinge having two facing interior sides, at least one interior side being covered with a material selected from a plurality of small hooks adapted to engage the brushed material on a strap and brushed material adapted to engage a plurality of small hooks on a strap;

said third hinge being attached to the proximal forearm piece and adapted to contact the dorsal wrist area and to provide adjustable tension with said strap means on the dorsal side of the wrist.

6. A splint as claimed in claim 5 wherein:

each said hinge includes an inner side adapted to contact the hand or forearm and an outer side facing said inner side;

any part of said malleable wire framework which is enclosed within said hinges is emplaced within the outer side of the hinge.

7. A splint as claimed in claim 1 further comprising:

a removable thumb support piece attached to said support framework.

8. A splint as claimed in claim 1 further comprising:

a thumb support piece attached to said support framework which comprises a malleable length of wire having two major sections, one section of which is adapted to be substantially aligned with the longitudinal axis of the thumb and another section of which is adapted to be substantially aligned with the thenar eminence;

a malleable metal strip adapted to surround the distal end of the thumb which is secured to said major thumb support sections; and, a pliant cushioning material enclosing at least a major portion of said thumb support framework.

9. A splint as claimed in claim 1 further comprising:

a volar MP joint support attached to said support framework.

10. A splint as claimed in claim 9 wherein:

said MP joint support is formed as a transverse extension of said palmar piece;

said MP joint support is at least partially enclosed by a pliant cushioning material, and further comprising:

adjustable dorsal strap means for holding said MP joint support into contact with a hand.

11. A splint as claimed in claim 10 further comprising:

a removable thumb support.

12. A splint as claimed in claim 11 wherein said removable thumb support further comprises:

a length of malleable wire adapted to provide support to the thumb and including an attached strip of malleable metal which is bent into a generally circular configuration adapted to support the distal end of the thumb;

a pliant cushioning material enclosing at least a major portion of said thumb support framework; and, means for removably attaching said thumb support to said splint.

13. A splint as claimed in claim 12 wherein said attachment means for said removable thumb support further comprises:
at least one patch of a plurality of small hooks adapted to engage brushed material adhered to at least one of said thumb support and said splint;
at least one patch of brushed material adapted to engage a plurality of small hooks adhered to at least one of said thumb support and said splint; and wherein,
said removable thumb support is attached to the palmar support and the MP extension.

14. A splint as claimed in claim 13 wherein said removable thumb support further comprises:
adjustable strap means for securing said removable thumb support to said splint.

15. A splint as claimed in claim 1 further comprising:
a dorsal MP extension stop comprising a manually bendable dorsal proximal phalangeal piece adapted to contact, cover and follow the curve of the proximal phalanges of the fingers; and,
a dorsal IP extension assist adapted for assisting extension of the IP joints of the fingers of a hand and which is secured to said dorsal MP extension stop.

16. A splint as claimed in claim 15 wherein:
said dorsal MP extension stop comprises a framework of wire formed as an extension of said palmar piece with a pliant cushioning material enclosing at least a major portion of said framework;
said IP extension assist comprises a transverse dorsal substantially U-shaped extension of said dorsal MP extension stop framework and elevated therefrom;
at least one finger sling for support of the distal end of a finger;
adjustable elastic tension means attached to each said finger sling;
means attached to said U-shaped extension for support of said finger sling and said elastic tension means;
means attached to said splint for attachment of said elastic tension means.

17. A splint as claimed in claim 16 wherein said IP extension assist further comprises:
said means attached to said U-shaped extension comprises at least one length of bendable wire having a loop at one end;
means for removably attaching each said bendable wire transversely and longitudinally to said U-shaped extension;
each said finger sling having means for removable attachment of said adjustable elastic tension means;
said adjustable elastic tension means attached to said finger sling being held by said loop of bendable wire and removably secured to said means attached to said splint for said elastic tension means.

18. A splint as claimed in claim 17 wherein:
said means for removable attachment of each said bendable wire to said U-shaped extension comprises two lengths of tubing each surrounding a leg of said U-shaped extension, each said length of tubing including a pair of aligned transverse apertures through which each said bendable wire can be removably inserted and which can be moved transversely along each leg by movement of each respective length of tubing;
each said adjustable elastic tension means further comprises a length of string which is attached at one end to a finger sling, is threaded through the end loop of said bendable wire, is extended over said U-shaped extension, and is attached to a length of elastic which is attached to said elastic tension securement means on said splint.

19. A splint as claimed in claim 18 further comprising as a major piece:
a thumb support.

20. A splint as claimed in claim 19 wherein said thumb support is removable and comprises:
a framework of a substantially L-shaped strip of bendable metal, one leg of which is substantially aligned with the longitudinal axis of the thumb, the other leg of which is bent into a substantially circular configuration to support the thumb;
a pliant cushioning material enclosing at least a major portion of said framework;
attachment means on said thumb support and on said splint for removably attaching said thumb support to said splint.

21. A splint as claimed in claim 20 wherein said removable thumb support further comprises:
a removable finger sling;
means attached to said thumb support for supporting said removable finger sling;
adjustable elastic tension means.

22. A splint as claimed in claim 21 wherein said removable thumb support further comprises:
a length of bendable wire having a loop at one end and a U-shaped bend at the other end, said U-shaped bend serving as an adjustable point of attachment of said bendable wire to said thumb support attachment means on said thumb support and on said splint;
said finger sling having means for removable attachment of said adjustable elastic tension means;
said adjustable elastic tension means attached to said finger sling being held by said loop of bendable wire and secured to said means attached to said splint for said elastic tension means.

23. A hand splint which does not contact the volar wrist comprising:
a manually bendable support framework with a pliant cushioning material enclosing at least a major portion of said framework;
said splint having an ulnar and a radial side corresponding to the contact of the splint with a forearm and comprising as major pieces;
a palmar piece adapted to extend under and across the palmar arch of a hand;
a proximal dorsal forearm piece adapted to contact the dorsal wrist and at least a portion of the dorsal forearm;
a dorsal hand piece extending between said palmar piece and said proximal dorsal forearm piece and adapted to contact and support the radial side of the hand and forearm;
said palmar piece, proximal dorsal forearm piece, and said hand piece forming a substantially "C" shape;
the top of the "C" including the palmar piece;
the back of the "C" adapted to extend along the radial side of the arm and including the dorsal hand piece;
the base of the "C" forming the proximal dorsal forearm piece and including a portion of the back of the "C" forming a radial extension adapted to extend along the radial side of the arm, a transverse extension adapted to extend across the dorsal forearm, and an ulnar extension adapted to extend along the ulnar side of the arm toward the dorsal wrist;

a thumb support attached to said support framework;

means for holding said major pieces together;

securement means for securing said splint to said hand and forearm; and, means to provide adjustable tension between said proximal dorsal forearm piece and said ulnar extension and adapted to contact only the dorsal side of the wrist.

24. A splint as claimed in claim 23 wherein:

said framework is formed of a single length of malleable wire;

said thumb support comprises a malleable length of wire having two major sections, one section of which is adapted to be substantially aligned with the longitudinal axis of the thumb and another section of which is adapted to be substantially aligned with the thenar eminence of the thumb;

said means to provide adjustable tension between said dorsal forearm piece and said ulnar extension and adapted to contact only the dorsal side of the wrist comprises an adjustable dorsal strap attached between said radial and ulnar extensions;

said securement means comprises adjustable strap means for extending ventrally across the proximal end of said proximal forearm piece and secured between said radial and ulnar extensions; and, adjustable strap means secured to said palmar piece and adapted to extend diagonally across the dorsal side of the hand from said radial side to said ulnar side of said splint and secured to said dorsal hand piece.

25. A splint as claimed in claim 24 wherein:

said strap means are comprised of an elastic strap;

and further comprising at least one area of a plurality of small hooks adapted to engage brushed material adhered to at least one of said strap and said palmar, dorsal hand, and proximal pieces; and, at least one area of brushed material adapted to engage a plurality of small hooks adhered to at least one of said strap and said palmar, dorsal hand, and proximal pieces.

26. A splint as claimed in claim 25 wherein said strap means further comprises:

a first lightly padded flexible hinge having two facing interior sides, at least one interior side being covered with a material selected from a plurality of small hooks adapted to engage the brushed material on a strap and brushed material adapted to engage a plurality of small hooks on a strap;

said first hinge being attached to the distal end of said palmar piece;

a second lightly padded flexible hinge having two facing interior sides, at least one interior side being covered with a material selected from a plurality of small hooks adapted to engage the brushed material on a strap and brushed material adapted to engage a plurality of small hooks on a strap;

said second hinge being attached to the proximal dorsal forearm piece for securing said splint around the ventral forearm;

a third lightly padded flexible hinge having two facing interior sides, at least one interior side being covered with a material selected from a plurality of small hooks adapted to engage the brushed material on a strap and brushed material adapted to engage a plurality of small hooks on a strap;

said third hinge being attached to the proximal forearm piece in the wrist area and adapted to provide adjustable tension on the dorsal side of the wrist.

27. A hand splint which does not contact the volar wrist comprising:

a manually bendable support framework with a pliant cushioning material enclosing at least a major portion of said framework;

said splint having an ulnar and a radial side corresponding to the contact of the splint with a forearm and comprising as major pieces;

a palmar piece adapted to extend under and across the palmar arch of a hand;

a proximal dorsal forearm piece adapted to contact the dorsal wrist and at least a portion of the dorsal forearm;

a dorsal hand piece extending between said palmar piece and said proximal dorsal forearm piece and adapted to contact and support the radial side of the hand and forearm;

said palmar piece, proximal dorsal forearm piece, and said dorsal hand piece forming a substantially "C" shape;

the top of the "C" including the palmar piece;

the back of the "C" adapted to extend along the radial side of the arm and including the dorsal hand piece;

the base of the "C" forming the proximal dorsal forearm piece and including a portion of the back of the "C" forming a radial extension adapted to extend along the radial side of the arm, a transverse extension adapted to extend across the dorsal forearm, and an ulnar extension adapted to extend along the ulnar side of the dorsal forearm toward the wrist;

a volar MP joint support attached to said support framework, said MP joint support being formed as a transverse extension of said palmar piece, and being at least partially enclosed by a pliant cushioning material;

an adjustable dorsal strap means for holding said MP joint support into contact with a hand;

a removable thumb support;

means for removably attaching said thumb support to said splint;

means for holding said major pieces together;

securement means for securing said splint to said hand and forearm; and, means adapted to provide adjustable tension on the dorsal side of the wrist.

28. A splint as claimed in claim 27 wherein:

said framework is formed of a single length of malleable wire;

said removable thumb support comprises a length of malleable wire adapted to provide support to the thumb and includes an attached strip of malleable metal which is bent into a generally circular configuration adapted to support the distal end of the thumb;

a pliant cushioning material enclosing at least a major portion of said thumb support framework;

said attachment means for said removable thumb support comprises at least one patch of a plurality of small hooks adapted to engage brushed material adhered to at least one of said thumb support and said splint;

at least one patch of brushed material adapted to engage a plurality of small hooks adhered to at least one of said thumb support and said splint;

said removable thumb support is attached to the palmar support and the MP extension;

adjustable strap means for securing said removable thumb support to said splint;

said means adapted to provide adjustable tension between said proximal dorsal forearm piece and said ulnar extension and adapted to contact the dorsal side of the wrist comprises an adjustable dorsal strap attached between said radial and ulnar extensions;

said securement means comprises adjustable strap means adapted to extend ventrally across the proximal end of said proximal forearm piece and secured between said radial and ulnar extensions; and, adjustable strap means secured to said palmar piece and adapted to extend diagonally across said dorsal hand from said radial side to said ulnar side and secured to said dorsal hand piece.

29. A splint as claimed in claim 28 wherein:

said strap means are comprised of an elastic strap;

at least one area of a plurality of small hooks adapted to engage brushed material adhered to at least one of said strap and said palmar, dorsal hand, and proximal pieces; and, at least one area of brushed material adapted to engage a plurality of small hooks adhered to at least one of strap and said palmar, dorsal hand, and proximal pieces.

30. A splint as claimed in claim 29 wherein said strap means further comprises:

a first lightly padded flexible hinge having two facing interior sides, at least one interior side being covered with a material selected from a plurality of small hooks adapted to engage the brushed material on a strap and brushed material adapted to engage a plurality of small hooks on a strap;

said first hinge being attached to the distal end of said palmar piece;

a second lightly padded flexible hinge having two facing interior sides, at least one interior side being covered with a material selected from a plurality of small hooks adapted to engage the brushed material on a strap and brushed material adapted to engage a plurality of small hooks on a strap;

said second hinge being attached to the proximal dorsal forearm piece adapted for securing said splint around the ventral forearm;

a third lightly padded flexible hinge having two facing interior sides, at least one interior side being covered with a material selected from a plurality of small hooks adapted to engage the brushed material on a strap and brushed material adapted to engage a plurality of small hooks on a strap;

said third hinge being attached to the proximal forearm piece and adapted to contact the dorsal wrist area and to provide adjustable tension with said strap means on the dorsal side of the wrist.

31. A hand splint which does not contact the volar wrist comprising:

a manually bendable support framework with a pliant cushioning material enclosing at least a major portion of said framework;

said splint having an ulnar and a radial side corresponding to the contact of the splint with a forearm and comprising as major pieces;

a palmar piece adapted to extend under and across the palmar arch of a hand;

a proximal dorsal forearm piece adapted to contact the dorsal wrist and at least a portion of the dorsal forearm;

a dorsal hand piece extending between said palmar piece and said proximal dorsal forearm piece and adapted to contact and support the radial side of the hand and forearm;

said palmar piece, proximal dorsal forearm piece, and said dorsal hand piece forming a substantially "C" shape;

the top of the "C" including the palmar piece;

the back of the "C" adapted to extend along the radial side of the arm and including the dorsal hand piece;

the base of the "C" forming the proximal dorsal forearm piece and including a portion of the back of the "C" forming a radial extension adapted to extend along the radial side of the arm, a transverse extension adapted to extend across the dorsal forearm, and an ulnar extension adapted to extend along the ulnar side of the arm toward the dorsal wrist;

a removable thumb support attached to said support framework;

a dorsal MP extension stop comprising a manually bendable dorsal proximal phalangeal piece adapted to contact, cover and follow the curve of the proximal phalanges of the fingers; and, a dorsal IP extension assist adapted for assisting extension of the IP joints of the fingers of a hand and which is secured to said dorsal MP extension stop;

means for holding said major pieces together;

securement means for securing said splint to a hand and forearm; and, means to provide adjustable tension between said proximal dorsal forearm piece and said ulnar extension and adapted to contact the dorsal side of the wrist.

32. A splint as claimed in claim 31 wherein:

said framework is formed of a single length of malleable wire;

said removable thumb support comprises a framework of a substantially L-shaped strip of bendable metal, one leg of which is adapted to be substantially aligned with the longitudinal axis of the thumb, the other leg of which is bent into a substantially circular configuration adapted to support the thumb;

a pliant cushioning material enclosing at least a major portion of said framework;

a removable finger sling;

means attached to said thumb support for supporting said removable finger sling;

adjustable elastic tension means attached to said finger sling;

said finger sling having means for attachment of said adjustable elastic tension means;

attachment means on said thumb support and on said splint for removably attaching said thumb support to said splint;

a length of bendable wire having a loop at one end and a U-shaped bend at the other end, said U-shaped bend serving as an adjustable point of attachment of said bendable wire to said attachment means on said thumb support and on said splint;

means attached to said splint for attachment of said elastic tension means;

said adjustable elastic tension means attached to said finger sling being held by said loop of bendable wire and secured to said means attached to said splint for said elastic tension means;

said means adapted to provide adjustable tension between said dorsal forearm piece and said ulnar extension and adapted to contact the dorsal side of the wrist comprises an adjustable dorsal strap attached to said proximal piece between said radial and ulnar extensions and adapted to contact the dorsal wrist;

said securement means comprises adjustable strap means extending ventrally across the proximal end of said proximal forearm piece and secured between said radial and ulnar extensions; and, adjustable strap means secured to said palmar piece and adapted to extend diagonally across said dorsal hand from said radial side to said ulnar side and secured to said dorsal hand piece.

33. A splint as claimed in claim 32 wherein:

said strap means are comprised of an elastic strap;

at least one area of a plurality of small hooks adapted to engage brushed material adhered to at least one of said strap and said palmar piece, dorsal hand piece, and proximal piece; and, at least one area of brushed material adapted to engage a plurality of small hooks adhered to at least one of said strap and said palmar, dorsal hand, and proximal pieces.

34. A splint as claimed in claim 33 wherein:

said means for attachment of each said bendable wire to said U-shaped extension comprises two lengths of tubing each surrounding a leg of said U-shaped extension, each said length of tubing including a pair of aligned transverse apertures through which each said bendable wire can be removably inserted and which can be moved transversely along each leg by movement of each respective length of tubing;

each adjustable elastic tension means attached to each said finger sling comprises a length of string which is attached at one end to a finger sling, is threaded through the end loop of said bendable wire, is extended over said U-shaped extension, and is attached to a length of elastic which is attached to said elastic tension securement means on said splint;

said strap means further comprises:

a first lightly padded flexible hinge having two facing interior sides, at least one interior side being covered with a material selected from a plurality of small hooks adapted to engage the brushed material on a strap and brushed material adapted to engage a plurality of small hooks on a strap;

said first hinge being attached to the distal end of said palmar piece;

a second lightly padded flexible hinge having two facing interior sides, at least one interior side being covered with a material selected from a plurality of small hooks adapted to engage the brushed material on a strap and brushed material adapted to engage a plurality of small hooks on a strap;

said second hinge being attached to the proximal dorsal forearm piece for securing said splint around the ventral forearm;

a third lightly padded flexible hinge having two facing interior sides, at least one interior side being covered with a material selected from a plurality of small hooks adapted to engage the brushed material on a strap and brushed material adapted to engage a plurality of small hooks on a strap;

said third hinge being attached to the proximal forearm piece and adapted to contact the dorsal wrist area to provide adjustable tension on the dorsal side of the wrist.

* * * * *